(12) United States Patent
Sebhat et al.

(10) Patent No.: US 7,834,042 B2
(45) Date of Patent: Nov. 16, 2010

(54) ANGIOTENSIN II RECEPTOR ANTAGONISTS

(75) Inventors: Iyassu K. Sebhat, Jersey City, NJ (US); Michael Man-chu Lo, Edison, NJ (US); Ravi P. Nargund, East Brunswick, NJ (US); Amjad Ali, Freehold, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/312,225

(22) PCT Filed: Dec. 11, 2007

(86) PCT No.: PCT/US2007/025231

§ 371 (c)(1),
(2), (4) Date: Jan. 27, 2010

(87) PCT Pub. No.: WO2008/076245

PCT Pub. Date: Jun. 26, 2008

(65) Prior Publication Data

US 2010/0152258 A1    Jun. 17, 2010

Related U.S. Application Data

(60) Provisional application No. 60/874,631, filed on Dec. 13, 2006.

(51) Int. Cl.
*A61K 31/41* (2006.01)
*C07D 257/04* (2006.01)

(52) U.S. Cl. ....................... 514/381; 548/250

(58) Field of Classification Search ............... 514/381; 548/250

See application file for complete search history.

(56) References Cited

U.S. PATENT DOCUMENTS

| | | | |
|---|---|---|---|
| 4,820,843 A | 4/1989 | Aldrich et al. |
| 4,845,079 A | 7/1989 | Luly et al. |
| 4,870,186 A | 9/1989 | Aldrich et al. |
| 4,874,867 A | 10/1989 | Aldrich et al. |
| 4,885,292 A | 12/1989 | Ryono et al. |
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,039,814 A | 8/1991 | Shuman et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,071,837 A | 12/1991 | Doherty et al. |
| 5,075,451 A | 12/1991 | Ocain et al. |
| 5,089,471 A | 2/1992 | Hanson et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,114,937 A | 5/1992 | Hamby et al. |
| 5,116,835 A | 5/1992 | Ruger et al. |
| 5,130,439 A | 7/1992 | Lo et al. |
| 5,138,069 A | 8/1992 | Carini et al. |
| 5,153,197 A | 10/1992 | Carini et al. |
| 5,206,374 A | 4/1993 | Lo |
| 5,310,928 A | 5/1994 | Lo et al. |
| 5,859,258 A | 1/1999 | Breen et al. |

FOREIGN PATENT DOCUMENTS

| | | | |
|---|---|---|---|
| WO | WO 2004/085428 | * | 7/2004 |
| WO | WO-2005/011646 A2 | | 2/2005 |
| WO | WO-2005/023182 A2 | | 3/2005 |
| WO | WO-2005/070868 A1 | | 8/2005 |

* cited by examiner

*Primary Examiner*—Kamal A Saeed
*Assistant Examiner*—Samantha L Shterengarts
(74) *Attorney, Agent, or Firm*—Paul J. Berman; Covington & Burling LLP

(57) ABSTRACT

A compound having the structure (Formula I), wherein Y is $-Y^1-Y^2-Y^3-Y^4-Y^5-$; $Y^1$ is C(O) or $C(R^1R^2)$; $Y^2$ is O, C(O), P(O)(OH) or $CH_2$, provided that when $Y^1$ is C(O), $Y^2$ is not C(O); $R^1$ is selected from the group consisting of hydrogen and $C_{1-4}$ alkyl; $R^2$ is selected from the pup consisting of hydrogen, $C_{1-4}$ alkyl, and $-OC(O)C_{1-4}$ alkyl; $Y^3$ is O, C(O) or $CH_2$, provided that when $Y^2$ is C(O), then $Y^3$ is not C(O), and further provided that when $Y^2$ is O, then $Y^3$ is not O; $Y^4$ is O or $CH_2$ or is absent, provided that when $Y^3$ is O, then $Y^4$ is not O; Y5 is $-(CH_2)_{1-2}-(X)_{0-1}-(CH_2)_{0-1}-$ or is absent; X is $-O-$ or $-CR^3R^4-$; and $R^3$ and $R^4$ are independently selected from the group consisting of hydrogen and $C_1-C_4$ alkyl; or a pharmaceutically acceptable salt thereof, which is useful for treating hypertension.

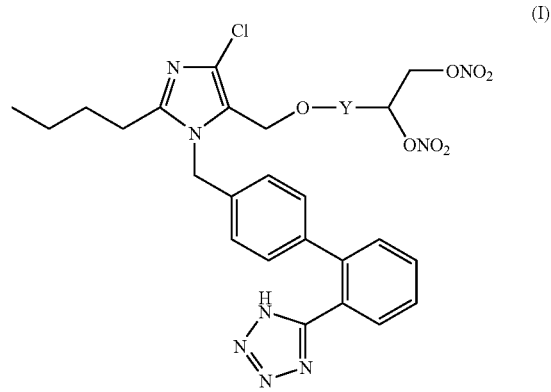

12 Claims, No Drawings

ANGIOTENSIN II RECEPTOR ANTAGONISTS

BACKGROUND OF THE INVENTION

U.S. Pat. No. 5,138,069 generically and specifically describes 2-butyl-4-chloro-1-[-p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,138,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

WO2005011646 describes angiotensin II receptor blocker nitroderivatives, pharmaceutical compositions containing them and their use for the treatment of cardiovascular, renal and chronic liver diseases, inflammatory processes and metabolic syndromes. The publication describes a variety of angiotensin receptor blocker compounds each of which are covalently linked in a variety of ways to a nitric oxide group. Specific examples include angiotensin receptor blockers with one covalently-linked nitric oxide group, and angiotensin receptor blockers with two independently-covalently-linked nitric oxide groups.

WO2005023182 describes nitrosated and nitrosylated cardiovascular compounds, and compositions comprising at least one nitrosated and nitrosylated cardiovascular compound and optionally at least one nitric oxide donor. The cardiovascular compound which is nitrosated or nitrosylated may be an aldosterone antagonist, an angiotensin II receptor antagonist, a calcium channel blocker, an endothelin antagonist, a hydralazine compound, a neutral endopeptidase inhibitor or a renin inhibitor. The nitric oxide donor may be selected from S-nitrosothiols, nitrites, nitrates, N-oxo-N-nitrosamines, furoxans, and sydnonimines.

WO2005070868 describes combination therapy for treating cyclooxygenase-2 mediated diseases or conditions at risk of thrombotic cardiovascular events which involves administering selected cyclooxygenase-2 inhibitor in combination with a nitric oxide donating compound such as 5,6-bis(nitrooxy)hexyl acetate, 6-hydroxyhexane-1,2-diyl dinitrate, 5-hydroxypentane-1,2-diyl dinitrate, (5R)-5,6-bis(nitrooxy) hexyl 4-nitrobenzoate, (5S)-5,6-bis(nitrooxy)hexyl 4-nitrobenzoate, (2R)-6-hydroxyhexane-1,2-diyl dinitrate, (2S)-6-hydroxyhexane-1,2-diyl dinitrate, (2S)-propane-1,2-diyl dinitrate, and (2R)-propane-1,2-diyl dinitrate.

SUMMARY OF THE INVENTION

The present invention includes angiotensin II receptor antagonist (2-butyl-4-chloro-1-{[2'-(1H-tetrazol-5-yl)biphenyl-4-yl]methyl}-1H-imidazol-5-yl)methyl(5R)-5,6-bis(nitrooxy)hexanoates, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist bis(nitroxy) derivatives having the general formula:

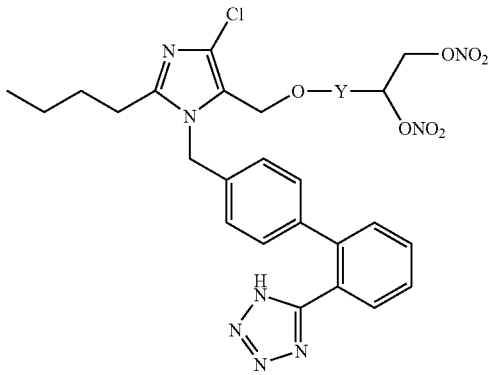

wherein

Y is —$Y^1$—$Y^2$—$Y^3$—$Y^4$—$Y^5$—;

$Y^1$ is C(O) or C($R^1R^2$);

$Y^2$ is O, C(O), P(O)(OH) or $CH_2$, provided that when $Y^1$ is C(O), $Y^2$ is not C(O);

$R^1$ is selected from the group consisting of hydrogen and $C_{1-4}$ alkyl;

$R^2$ is selected from the group consisting of hydrogen, $C_{1-4}$ alkyl, and —OC(O)$C_{1-4}$ alkyl;

$Y^3$ is O, C(O) or $CH_2$, provided that when $Y^2$ is C(O), then $Y^3$ is not C(O), and further provided that when $Y^2$ is O, then $Y^3$ is not O;

$Y^4$ is O or $CH_2$ or is absent, provided that when $Y^3$ is O, then $Y^4$ is not O;

$Y^5$ is —$(CH_2)_{1-2}$—$(X)_{0-1}$—$(CH_2)_{0-1}$— or is absent;

X is —O— or —$CR^3R^4$—; and $R^3$ and $R^4$ are independently selected from the group consisting of hydrogen and $C_1$-$C_4$ alkyl;

or a pharmaceutically acceptable salt thereof.

In one embodiment, $Y^1$ is C(O), and all other variables are as previously defined.

In another embodiment, $Y^2$ is $CH_2$, and all other variables are as previously defined.

In another embodiment, $Y^3$ is $CH_2$, and all other variables are as previously defined.

In another embodiment, $Y^4$ is $CH_2$, and all other variables are as previously defined.

In another embodiment, $Y^5$ is absent, and all other variables are as previously defined.

The compounds of the present invention are angiotensin II receptor antagonist (2-butyl-4-chloro-1-{[2'-(1H-tetrazol-5-yl)biphenyl-4-yl]methyl}-1H-imidazol-5-yl)methyl(5R)-5,6-bis(nitroxy) hexanoates, or a pharmaceutically acceptable salt thereof, having the structure

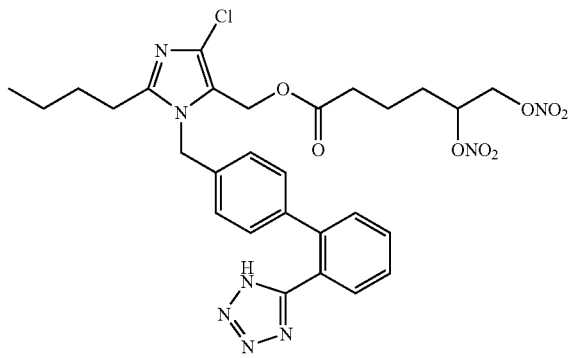

In one embodiment, the compound has the structure:

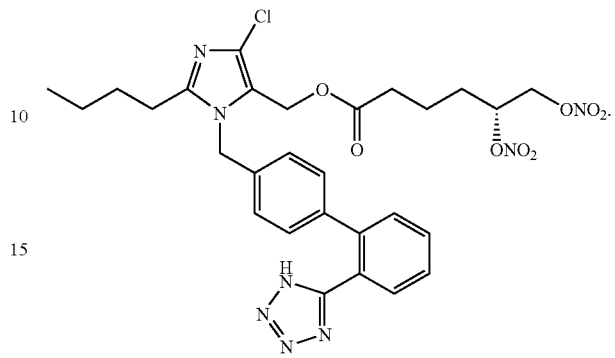

In another embodiment, the compound has the structure:

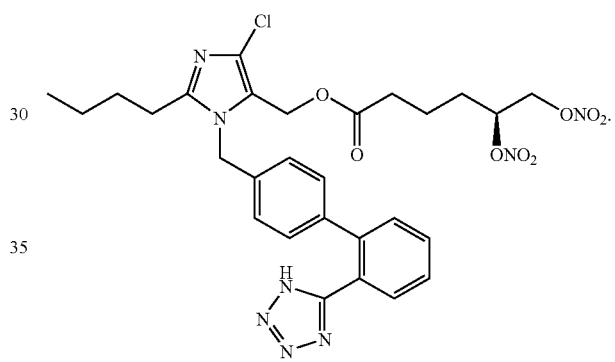

The dinitrate compounds of the invention provide enhanced NO release over mononitrate analogs. While mononitrate compounds orally dosed to rats result in reactive nitrite species circulating in plasma with maximal concentration in the 0.5-2.8 μM range, similar dosing of compounds of the present invention result in an unexpectedly large increase in circulating nitrite concentrations. A consideration of stoichiometry leads to an expectation of a doubling of nitrite levels. Compounds of the invention, however, provide a nitrite level increase more than two fold. Also, in vitro, tissue-based measure of vessel relaxation, determined in rabbit aortic slices, show large improvements in $EC_{50}$ (molar concentration of compound which produces 50% of the maximum possible response for that compound) compared to mononitrates which are greater than the increase expected based on the stoichiometric relationship.

Biochemical evidence for the generation of NO in vivo in response to test compound administration was obtained from studies in Sprague-Dawley (SD) rats. Administration of test compound to fasted SD rats (40 mpk, PO) results in the appearance of reactive nitrogen species (RNS), assessed using the diaminonapthalene derivitization (DAN) assay. Compounds 1-2 as numbered and identified in Table 1 below were tested. Compound 2 showed improved RNS levels.

TABLE 1

| Structure | Compound Number |
| --- | --- |
| 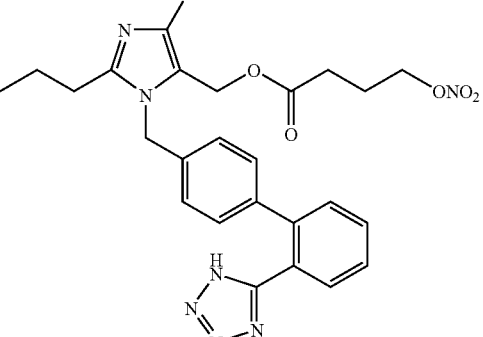 | 1 |
| 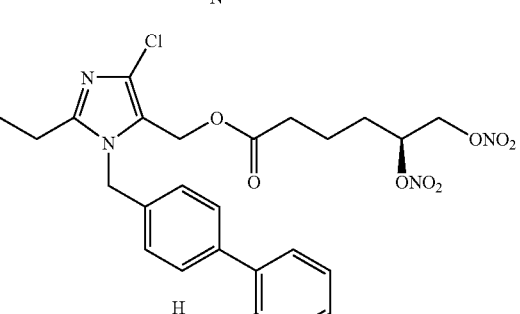 | 2 |

RNS levels for the tested compounds are shown below in Table 2:

TABLE 2

| Time (h) | 1 | 2 |
| --- | --- | --- |
| 0 | 0.7 + 0.12 | 0.6 + 0.11 |
| 1 | 1.1 + 0.22 | 9.8 + 3.8 |
| 3 | 1.1 + 0.26 | 3.1 + 2.48 |
| 6 | 1.1 + 0.34 | 2.1 + 1.65 |
| 24 | 1.7 + 0.15 | 0.5 + 0.26 |

Angiotensin II Receptor Antagonists—Therapeutic Uses—Method of Using

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl)methyl]-imidazole-5-carboxylic acid is the active metabolite of 2-butyl-4-chloro-1-[p-(o-1H-tetrazol-5-ylphenyl)-benzyl]imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

Compounds of the invention can be prepared using losartan potassium salt as the starting material, forming the appropriate dinitrate as in Step A, forming the corresponding carboxylic acid as in Step B, reacting the carboxylic acid with losartan potassium as in Step C, and subsequently forming the desired salt as is Step D.

EXAMPLE 1

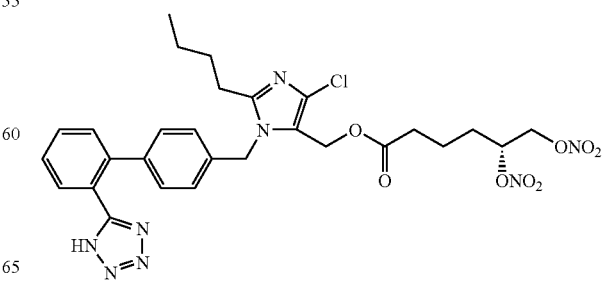

Step A: (2R)-6-hydroxyhexane-1,2-diyl dinitrate

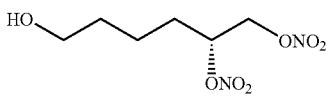

The title compound was prepared as described in WO2005070868(A1).

Step B: (5R)-5,6-bis(nitrooxy)hexanoic acid

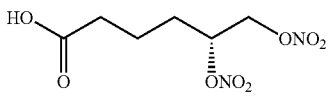

A mixture of (2R)-6-hydroxyhexane-1,2-diyl dinitrate (13.5 g, 60.2 mmol) and sodium periodate (38.74 g, 181 mmol) was suspended in a mixture of water (250 mL), acetonitrile (250 mL), and chloroform (250 mL). Ruthenium oxide hydrate (0.813 g, 6.11 mmol) was then added, turning the reaction bright yellow. After 16 hours, the reaction mixture was concentrated in vacuo to remove the organic solvents. The residue was extracted with dichloromethane (3×200 mL), and the combined organic extracts were washed with brine, dried (magnesium sulfate), and concentrated in vacuo to afford the crude product. Chromatography over silica eluting with 0-5% methanol in dichloromethane afforded the title compound as a yellow liquid. $^1$H NMR (500 MHz, CDCl$_3$) δ 5.26-5.33 (m, 1H), 4.76 (dd, J=3.1, 12.9 Hz, 1H), 4.49 (dd, J=6.4, 13.0 Hz, 1H), 2.45 (t, J=5.8 Hz, 2H), 1.72-1.88 (m, 4H).

Step C: (2-butyl-4-chloro-1-{[2'-(2H-tetrazol-5-yl)biphenyl-4-yl]methyl}-1H-imidazol-5-yl)methyl (5R)-5,6-bis(nitrooxy)hexanoate

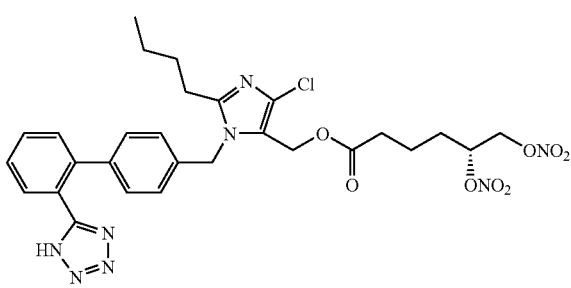

To a dichloromethane (50 mL) suspension of Losartan potassium (4.72 g, 10.24 mmol), (5R)-5,6-bis(nitrooxy)hexanoic acid (1.23 g, 5.16 mmol), and 4-dimethylaminopyridine (0.075 g, 0.614 mmol) was added N-methylmorpholine (1.2 mL, 10.91 mmol), followed by N-(3-dimethylaminopropyl)-N'-ethylcarbodiimide hydrochloride (1.2 g, 6.26 mmol). After 2 hours, the reaction mixture was mixed with pH 5 buffer (sodium phosphate monobasic/sodium phosphate dibasic, 250 mL) and extracted with ethyl acetate. The combined organic extracts were washed with brine, dried (magnesium sulfate), and concentrated in vacuo. Chromatography over silica eluting with 2-12% methanol/dichloromethane afforded the title compound as a white solid (2.485 g, 3.86 mmol, 74.8% yield). $^1$H NMR (500 MHz, CD$_3$CN) δ 7.69 (dd, J=1.1, 7.6 Hz, 1H), 7.64 (dt, J=1.3, 7.6 Hz, 1H), 7.53 (dt, J=1.1, 7.6 Hz, 1H), 7.49 (d, J=7.8 Hz, 1H), 7.09 (d, J=8.3 Hz, 2H), 6.91 (d, J=8.3 Hz, 2H), 5.27 (dq, J=2.8, 6.3 Hz, 1H), 5.15 (s, 2H), 4.95 (s, 2H), 4.75 (dd, J=2.8, 12.8 Hz, 1H), 4.51 (dd, J=6.1, 12.9 Hz, 1H), 2.48 (t, J=7.7 Hz, 2H), 2.08 (t, J=7.3 Hz, 2H), 1.5-1.7 (m, 6H), 1.28 (pent, J=7.4 Hz, 2H), 0.83 (t, J=7.5 Hz, 3H). LCMS: m/e 643.2 (M+H).

Step D: potassium 5-(4'-{[5-({[(5R)-5,6-bis(nitrooxy)hexanoyl]oxy}methyl)-2-butyl-4-chloro-1H-imidazol-1-yl]methyl}biphenyl-2-yl)tetrazol-2-ide

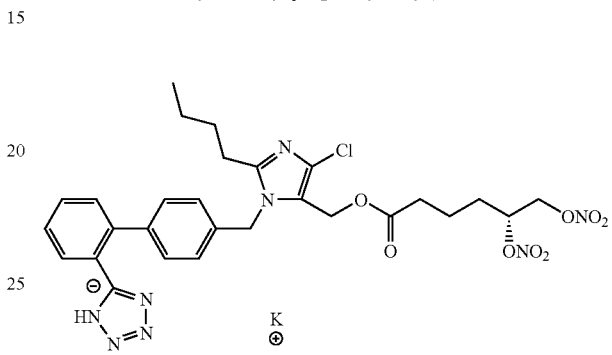

To a mixture of (2-butyl-4-chloro-1-{[2'-(2H-tetrazol-5-yl)biphenyl-4-yl]methyl}-1H-imidazol-5-yl)methyl (5R)-5,6-bis(nitrooxy)hexanoate (349.3 mg, 0.543 mmol) and potassium carbonate (922.7 mg, 6.68 mmol) was added 2-propanol (25 mL). After 30 minutes, the reaction mixture was filtered and concentrated in vacuo. More washings of the residual solids were performed with ethyl acetate, and the product was precipitated with hexanes. Repeating the cycle twice and drying of the solid in vacuo afforded the title compound as a white solid. $^1$H NMR (500 MHz, CD$_3$CN) δ 7.62 (dd, J=1.3, 7.3 Hz, 1H), 7.39 (dt, J=1.6, 7.4 Hz, 1H), 7.36 (dt, J=1.6, 7.3 Hz, 1H), 7.31 (dd, J=1.7, 7.4 Hz, 1H), 7.14 (d, J=8.2 Hz, 2H), 6.83 (d, J=8.2 Hz, 2H), 5.27 (dq, J=2.6, 6.4 Hz, 1H), 5.13 (s, 2H), 4.96 (s, 2H), 4.76 (dd, J=2.6, 12.9 Hz, 1H), 4.51 (dd, J=6.1, 12.9 Hz, 1H), 2.54 (t, J=7.7 Hz, 2H), 2.05 (dt, J=1.8, 7.1 Hz, 2H), 1.48-1.68 (m, 6H), 1.30 (pent, J=7.5 Hz, 2H), 0.85 (t, J=7.3 Hz, 3H). LCMS: m/e 643.2 (M+H).

What is claimed is:
1. A compound having the structure

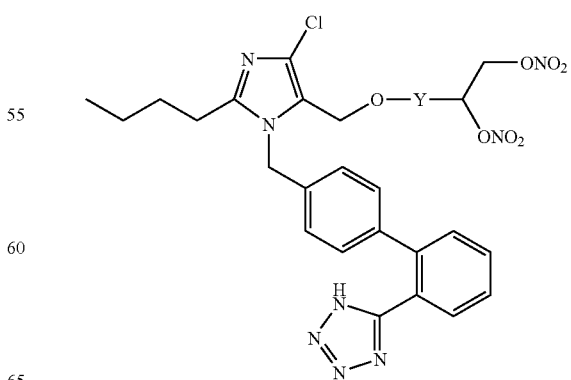

wherein
Y is —$Y^1$—$Y^2$—$Y^3$—$Y^4$—$Y^5$—;
$Y^1$ is C(O) or C($R^1R^2$);
$Y^2$ is O, C(O), P(O)(OH) or $CH_2$, provided that when $Y^1$ is C(O), $Y^2$ is not C(O);
$R^1$ is selected from the group consisting of hydrogen and $C_{1-4}$ alkyl;
$R^2$ is selected from the group consisting of hydrogen, $C_{1-4}$ alkyl, and —OC(O)$C_{1-4}$ alkyl;
$Y^3$ is O, C(O) or $CH_2$, provided that when $Y^2$ is C(O), then $Y^3$ is not C(O), and further provided that when $Y^2$ is O, then $Y^3$ is not O;
$Y^4$ is O or $CH_2$ or is absent, provided that when $Y^3$ is O, then $Y^4$ is not O;
$Y^5$ is —$(CH_2)_{1-2}$—$(X)_{0-1}$—$(CH_2)_{0-1}$— or is absent;
X is —O— or —$CR^3R^4$—; and
$R^3$ and $R^4$ are independently selected from the group consisting of hydrogen and $C_1$-$C_4$ alkyl;
or a pharmaceutically acceptable salt thereof.

2. A compound of claim 1, wherein $Y^1$ is C(O).
3. A compound of claim 1, wherein $Y^2$ is $CH_2$.
4. A compound of claim 1, wherein $Y^3$ is $CH_2$.
5. A compound of claim 1, wherein $Y^4$ is $CH_2$.
6. A compound of claim 1, wherein $Y^5$ is absent.
7. A compound having the structure

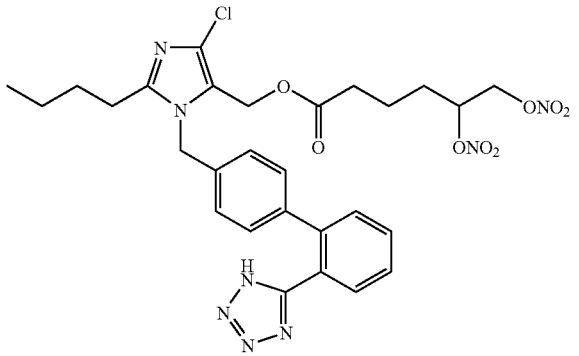

or a pharmaceutically acceptable salt or hydrate thereof.

8. A compound of claim 7 having the structure

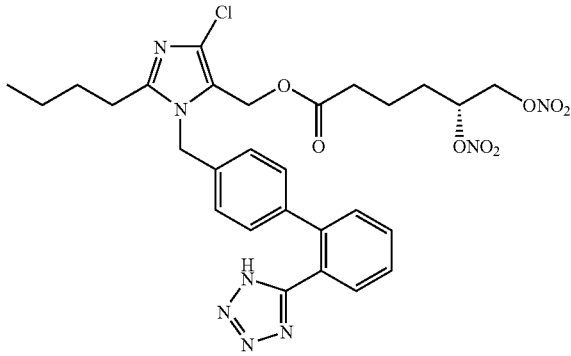

or a pharmaceutically acceptable salt or hydrate thereof.

9. A compound of claim 7 having the structure

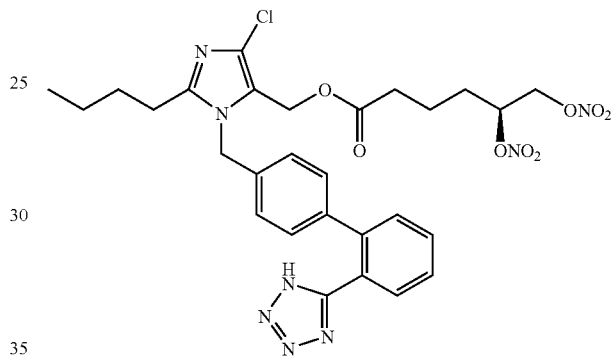

or a pharmaceutically acceptable salt or hydrate thereof.

10. A pharmaceutical composition comprising a compound of claim 7 and a pharmaceutically acceptable carrier.
11. A pharmaceutical composition comprising a compound of claim 7, a diuretic and a pharmaceutically acceptable carrier.
12. A method for treating hypertension in a patient which comprises administering to the patient a therapeutically effective amount of the composition of claim 10.

* * * * *